United States Patent [19]

Martin et al.

[11] Patent Number: 4,758,597

[45] Date of Patent: Jul. 19, 1988

[54] CARENADIOL AND DERIVATIVES

[75] Inventors: Arnold R. Martin; Paul F. Consroe; Vibhakar J. Shah, all of Tucson, Ariz.

[73] Assignee: University Patents, Inc., Westport, Conn.

[21] Appl. No.: 50,123

[22] Filed: May 15, 1987

[51] Int. Cl.⁴ ............................................. A61K 31/05
[52] U.S. Cl. .................................... 514/729; 568/734
[58] Field of Search ................. 568/734, 731; 514/729

[56] References Cited

U.S. PATENT DOCUMENTS 2,834,814  5/1958  Bain et al. ........................... 568/734
4,282,248  8/1981  Mechoulam et al. ............... 568/734

FOREIGN PATENT DOCUMENTS 1543647  11/1967  France ............................... 568/734

OTHER PUBLICATIONS

Mechoulam et al., *J.A.C.S.*, vol. 89, pp. 4552–4554, (1967).
Consroe et al., "Marihuana' 84, Proceedings of the Oxford Symposium an Cannabis, pp. 705–712, (1984).
Consroe et al., *J. Clin. Pharmacol*, vol. 21, pp. 4285–4365, (1981).

*Primary Examiner*—James H. Reamer
*Attorney, Agent, or Firm*—George M. Yahwak

[57] ABSTRACT

The present invention relates to new synthetic compounds of the cannabinoid class, specifically carenadiol and its derivatives. This compound and its derivatives have been shown to have biological activity which indicates their usefulness in the treatment of patients with various neurological disorders.

9 Claims, No Drawings

CARENADIOL AND DERIVATIVES

Naturally occurring materials of plant origin have been used on numerous prior occasions for the treatment of various pathological states in man. The occasion which has received the greatest publicity in recent times has been the use of marajuana and marajuana-derived chemicals in the treatment of various side effects experienced by patients during cancer chemotherapy.

One compound derived from marajuana and often used for its potential therapeutic utility is (−)-Cannabidiol, or (−)-CBD, a natural and major cannabinoid found in Cannabis. In man, the drug has been shown to have antiepileptic efficacy and possibly antidystonic activity, while exhibiting no recognized and undesired side effects. It also has no cannabimimetic activity often associated with Cannabis or its neutral major psychoactive ingredient, (−)-delta-9-tetrahydrocannabinol, commonly called (−)-delta-9-THC or delta-1-THC.

In laboratory animals, (−)-CBD has selectivity of anticonvulsant action relative to neurotoxic effects, and is inactive in those models that predict cannabimimetic activity. This dicohtomy of action between (-)-CBD and (-)-delta-9-THC has led to many investigations of the structure activity relationships in cannabinoids. Most of these studies, however, have been carried out with the THC analogs and with laboratory animal models of cannabimimetic activity. Thus, virtually all knowledge of cannabinoid structure activity relationships is based upon the physchoactive component of Cannabis-like effect. On the other hand, some studies evaluating the anticonvulsant effects of CBD stereoisomers and putative metabolites in mice have been reported.

Our own research which led to the making of the present invention has been an interdisciplinary research project to evaluate the antiepileptic potential and structure activity relationships of new synthetic CBD analogues (see, for example, Anticonvulsant effects of cannabidiol stereoisomers and analogs in rats, *Marijuana '84 Proceedings of the Oxford Symposium on Cannabis*; IRL Press, pages 705–712[1985]; Antiepileptic potential cannabidiol analogs, *J Clin Pharmacol* 21:428–436[1981]; and Therapeutic potential of cannabinoids in neurological disorders, *Cannabinoids as Therapeutic Agents*, CRC Press, pages 21–49[1986].

Of the various compounds which were synthesized and tested for the first time, the compound which appeared to be the most active, and thus by definition the compound of choice if one needs to be named specifically, is a compound we have named (±)-Carenadoil. This is a newly synthesized compound of the cannabinoid class which is chèmically more closely related to the cannabidiol (CBD) type of compound than to the tetrahedrocannabinol (THC) or hexahydrocannabinol type of cannabinoids. Structurally, this compound may be depicted by the general formula:

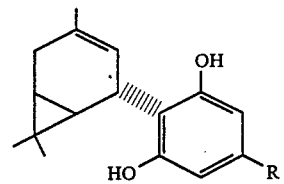

in which R is a lower alkyl having the formula $C_5H_{11}$. The family of compounds according to the present invention, however, are those compounds of the general formula wherein R is a lower alkyl containing from 1 to 9 carbon atoms including those having different isomeric forms such as, for example, i-butyl, n-butyl, and t-butyl which would all be classified as an alkyl containing 4 carbon atoms.

In general, the compounds of the present invention, and specifically those preferred compounds described in Table 1, were prepared from Car-4-en-3 -ol of the formula:

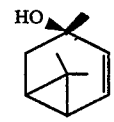

and corresponding 5-alkyl resorcinols of the formula:

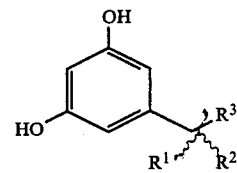

2a. $R^1 = R^2 = H$, $R^3 = C_4H_9$
b. $R^1 = R^2 = CH_3$, $R^3 = C_6H_{13}$ following the recognized procedures of Patrzilka (*Helv. Chim. Acta.*, 50:719, 1967). The synthesis of Car-4-en-3 -ol was accomplished following the procedure outlined by Uzarewicz and Sientek (Roczniki Chemmi, *An. Soc. Chim. Polonorum*, 51:181, 1977) from 3 4-epoxy carane (see *Tetrahedron Letters* 51:4451, 1969). The 5-alkyl resorcinols were synthesized in accordance with the methods developed by Dominianni (*J. Org. Chem.*, 42:344, 1977). The following example illustrates the experimental conditions used for the condensation of these compounds:

EXAMPLE 1

To a stirring solution of the 5-alkyl resorcinol (formula 2) (a : 0.811g, 4.5 mM; b : 1.0635g, 4.5 mM) in 25 ml dry dichloromethane (dist. over calcium hydride), a solution of Car-4-en-3 -ol (0.761g, 5mM) in 25 ml of dry dochloromethane and N, N-dimethylformamide dineopentyl acetal (1.3882g, 6mM) were added in order under Nitrogen atomosphere. The reaction mixture was stirred at room temperature for 60–63 hrs. Reaction mixture was poured into 50 ml of chilled water. The aqueous layer was extracted with 25 ml of dichloromethane. The dichloromethane layers were combined, washed with brine and dried over sodium sulfate. Evaporation of the solvent provided reddish brown oil which was further purified by column chromatography using silicagel in each case. Both 3a and 3b were characterized by IR, $^1$H NMR, $^{13}$C NMR, MS and elemental analysis.

Isolated yield of (+)-5a=0.335 gm (20%)
Isolated Yield of (+)-5b=0.515 gm (20%)

Because of the activity we have noted in animal models using this compound, we propose that (−)-Carenadiol, its derivatives, and its analogues may have specific utility for the treatment of patients which various neurological disorders including epilepsy (e.g. partial seizures and generalized seizures of the grand mal type of epilepsy), hyperkinetic movement disorders (e.g., the dystonias, the tardive dyskinesias, and choreoathetosis), skeletal muscle spasticity (e.g., as seen in multiple sclerosis and spinal cord injuries), and action (intention) tremor (e.g., as seen in multiple sclerosis and other disorders).

With regard to the potential use of this family of compounds in the treatment of epilepsy, (+)-Carenadiol was evaluated in the audiogenic seizure (AGS-susceptible) rat model of eilepsy to assess its anticonvulsant activity, and the rat rotorod (ROT) paadigm was used to assess differential neurotoxicity (i.e., reflecting mainly sedation and/or incoordination), of this family of compounds. The result of this evaluation are reported in Table 1.

For AGS tests, male and female, 150–225 gm, genetically epilepsy prone rats were used. For ROT tests, male and female, 150–225 gm. rats were used. CBD analogs (suspended in a vehicle of 10% polysorbate 80 and 90% distilled water) were injected intravenously and rats were tested 15 minutes later (a peak-effect time for both tests). In the AGS test, responses to sound were recorded as the presence or absence of seizure (i.e., generalized clonus or clonus and generalized flexion). In the ROT test, effects were measured as the ability or inability (i.e., neurotoxicity) of trained rats to remain on a revolving drum (rotorod) for 60 seconds.

Separate groups of 10–15 rats were used for each doses of drug tested and, typically, 3–6 doses of each analog were used for each AGS and ROT test. For appropriate dose-response data, median effective anticonvulsant (ED50) and neurotoxic (TD50) doses and regression line parameters were calculated by computer-assisted probit analysis. Subsequent calculations of 95% confidence limits (CL) and comparisons between slopes and median doses (i.e., ED50 and TD50 potency comparisons) were carried out using the method of Litchfield and Wilcoxon [*J. Pharmacol Exp Ther* 96:99–133(1949)]. Protective indexes (PI =ROT-TD50/AGS-ED50) also were calculated.

TABLE 1

Dose-Response Data of Standard Anticonvulsants and CBD Analogs in ROT and AGS Tests[a]

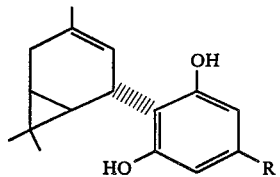

| Compound | R | ROT | AGS | PI |
|---|---|---|---|---|
| (+)-5a | C$_5$H$_{11}$ | 99.8 (90.4–110.1) | 18.1 (16.2–20.3) | 5.5 |
| (+)-5b | 1,1-DMH | 3.7 (3.3–4.1) | 3.4 (3.0–3.9) | 1.1 |
| Phenobarbital | | 28.9 | 10.8 | |
| Carbamazepine | | (26.0–32.2) 33.9 (32.6–35.4) | (8.5–13.8) 12.8 (9.7–16.9) | 2.7 2.7 |
| Phenytoin | | 23.9 (22.3–25.6) | 14.7 (11.1–19.6) | 1.6 |

[a]Median toxic (TD50) and effective (ED50) doses and 95% confidence limits (in parentheses) are in mg/Kg, iv PI = protective index = ROT-TD50/AGS-ED50. Ratios refer to the number of rats protected against AGS or number of rats toxic/number of rats tested (at the iv dose listed). DMH = dimethylheptyl.

The compounds of the present invention can be formulated into various pharmaceutical compositions for the treatment of various neurological disorders in mammals. These compositions will comprise at least one comound of the present invention and/or at least one pharmacologically compatible salt thereof in admixture with a solid or liquid pharmaceutical diluent or carrier for enteral or parenteral administration. As injection medium, water is preferably used which contains the usual additives for injection solutions, such as stabilizing agents, solubilizing agents, and buffers. Among additives of this type are, for example, tartrate and citrate buffers, ethanol, complex-forming agents such as ethylene-diamine-tetraacetic acid and the nontoxic salts thereof, and high molecular weight polymers such as liquid polyethylene oxide for viscosity regulation. Solid carrier materials include, for example, starch, lactose, mannitol, methyl cellulose, talc, highly dispersed silicic acid, high molecular weight fatty acids such as stearic acid, gelatine, agar-agar, calcium phosphate, magnesium stearate, animal and vegetable fats, and solid high molecular weight polyalkylene glycol polymers such as polyethylene glycols, and other compatible adjuvants routinely used for the preparation of medicaments. Compositions suitable for oral administration can, if desired, contain flavoring and/or sweetening agents.

In addition, the compounds of the present invention may be prepared as pharmacologically compatible salts, for example, as salts of these compounds physiologically acceptable inorganic and organic acids such as hydrochloric acid, sulfuric acid, phosphoric acid, fumaric acid, oxalic acid, citric acid, etc., and the quaternary ammonium compounds.

These are conventionally prepared by esterification of the phenolic or amino acid groups, and subsequent preparation in the usual manner, for example by neutralization of the free bases with pharmacologically compatible inorganic or organic acids, such as hydrochloric, sulphuric, phosphoric, hydrobromic, acetic, lactic, citric, malic, salicyclic, malonic, maleic, and succinic acids.

The compounds of the present invention can be formulated into various dosage forms for oral, parenteral or rectal administration. Included in these dosage forms are tablets, capsules, suspensions, emulsions, syrups, suppositories, and other liquid and solid compositions known to those skilled in the pharmaceutical formulation arts.

The individual dosage of the compounds according to the present invention used depends upon the nature and severity of the disease state, as well as the conventional concerns such as body weight, age, and overall health of the patient to be treated. In an individual of average weight and health, dosages of between 10 and 200 mg of the compounds of the present invention will normally be administered per kilogram of body weight.

It will be appreciated by those skilled in the art that many variations may be made to individual features of the present invention without departing from the overlying principle described for the various derivatives, compositions, and methods described in this specification of invention. Accordingly, the present invention is not to be considered as limited to the specific examples and compounds described previously, but the present invention is properly extended to encompass those variations which may be made to individual features of the described invention which do not depart from the overlying principles of the invention.

Having thus described our invention and the manner and process for the manufacture and use of the invention in such full, clear, concise, and exact terms as to enable any person skilled in the art to which it pertains, or with which it is most nearly connected, to make and use the same,

We claim:

1. A compound of the formula

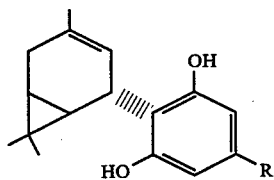

wherein R is a lower alkyl containing from 1 to 9 carbon atoms, and the pharmaceutically acceptable salt thereof.

2. The compound according to claim 1 wherein R is a lower alkyl of the formula $C_5H_{11}$.

3. The compound according to claim 1 wherein R is 1,1,-dimethylheptyl.

4. The pharmaceutical composition comprising a compound of the formula

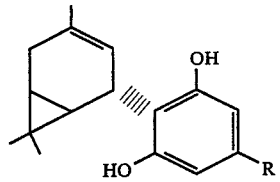

wherein R is a lower alkyl containing from 1 to 9 carbon atoms, and the pharmaceutically acceptable salt thereof.

5. The composition according to claim 4 in which R is a lower alkyl of the formula $C_5H_{11}$.

6. The composition according to claim 4 wherein R is 1,1-dimethylheptyl.

7. A method for the treatment of a neurological disorder which comprises administering to an animal having a neurological disorder an amount sufficient to bring about such treatment of a pharmaceutical composition comprising a compound of the formula

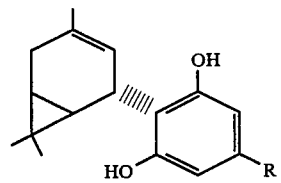

wherein R is a lower alkyl containing from 1 to 9 carbon atoms, and the pharmaceutically acceptable salt thereof.

8. The method of claim 7 wherein R is a lower alkyl of the formula $C_5H_{11}$.

9. The method of claim 7 wherein R is 1,1-dimethylheptyl.

* * * * *